(12) United States Patent
Michelson

(10) Patent No.: US 7,972,381 B2
(45) Date of Patent: *Jul. 5, 2011

(54) SPINAL IMPLANT SURFACE CONFIGURATION WITH A PROJECTION HAVING A BACK CUT

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 530 days.

This patent is subject to a terminal disclaimer.

(21) Appl. No.: 10/683,071

(22) Filed: Oct. 10, 2003

(65) Prior Publication Data

US 2004/0117018 A1    Jun. 17, 2004

Related U.S. Application Data

(63) Continuation of application No. 09/457,228, filed on Dec. 8, 1999, now Pat. No. 6,827,740.

(51) Int. Cl.
*A61F 2/44* (2006.01)
(52) U.S. Cl. ..................... 623/17.11
(58) Field of Classification Search .... 623/17.11–17.16, 623/23.26
See application file for complete search history.

(56) References Cited

U.S. PATENT DOCUMENTS

| | | | |
|---|---|---|---|
| 4,349,921 A | 9/1982 | Kuntz | |
| 4,531,244 A | 7/1985 | Hamas | |
| 4,673,409 A | 6/1987 | Van Kampen | |
| 4,795,472 A | 1/1989 | Crowninshield et al. | |
| 4,834,757 A | 5/1989 | Brantigan | |
| 4,865,603 A | 9/1989 | Noiles | |
| 4,944,763 A | 7/1990 | Willert et al. | |
| 4,955,907 A | 9/1990 | Ledergerber | |
| 5,019,107 A | 5/1991 | Schelhas | |
| 5,306,308 A | 4/1994 | Gross et al. | |
| 5,425,772 A | 6/1995 | Brantigan | |
| 5,522,899 A | 6/1996 | Michelson | |
| 5,553,476 A | 9/1996 | Oehy et al. | |
| 5,593,409 A | 1/1997 | Michelson | |
| 5,609,635 A | 3/1997 | Michelson | |
| 5,683,464 A | 11/1997 | Wagner et al. | |

(Continued)

FOREIGN PATENT DOCUMENTS

EP    0 637 440    2/1995

(Continued)

*Primary Examiner* — Bruce E Snow
(74) *Attorney, Agent, or Firm* — Martin & Ferraro, LLP

(57) ABSTRACT

The present invention is a specialized implant having opposed surfaces for engaging each of the vertebral bodies adjacent a disc space into which the implant is implanted. The surface comprises arrayed projections having at least one forward facing facet directed at least in part toward the leading end of the implant and at least one rearward portion directed at least in part toward the opposite trailing end of the implant. Each of the forward facet and rearward portion has a length and a slope. The length of the forward facet is longer than the length of the rearward facet. The slope of the rearward facet is steeper than the slope of the forward facet. The surface projections also have opposed side facets directed generally toward the sides of the implant. The side facets are located between the forward facet and rearward facet and converge toward each other in a direction away from the base of the surface projections. The surface may also include projections having left and right forward side facets and a rearward facet. The surface further may include projections having left and right rearward side facets and a forward facet.

110 Claims, 9 Drawing Sheets

U.S. PATENT DOCUMENTS

| | | |
|---|---|---|
| 5,713,899 A | 2/1998 | Marnay et al. |
| 5,716,412 A | 2/1998 | DeCarlo, Jr. et al. |
| 5,755,799 A | 5/1998 | Oehy et al. |
| 5,860,973 A | 1/1999 | Michelson |
| 5,865,845 A | 2/1999 | Thalgott |
| 5,888,227 A | 3/1999 | Cottle |
| 5,899,941 A | 5/1999 | Nishijima et al. |
| 5,989,289 A | 11/1999 | Coates et al. |
| 6,019,793 A | 2/2000 | Perren et al. |
| 6,080,158 A | 6/2000 | Lin |
| 6,143,033 A | 11/2000 | Paul et al. |
| 6,174,334 B1 | 1/2001 | Suddaby |
| 6,190,414 B1 | 2/2001 | Young et al. |
| 6,258,125 B1 | 7/2001 | Paul et al. |
| 6,325,827 B1 * | 12/2001 | Lin ............................... 623/17.16 |
| 6,425,920 B1 | 7/2002 | Hamada |
| 6,432,106 B1 * | 8/2002 | Fraser ............................... 606/61 |
| 6,482,233 B1 | 11/2002 | Aebi et al. |
| 6,511,509 B1 | 1/2003 | Ford et al. |
| 6,592,624 B1 * | 7/2003 | Fraser et al. ............... 623/17.16 |
| 6,660,038 B2 | 12/2003 | Boyer, II et al. |
| 2002/0068978 A1 * | 6/2002 | Camino et al. ............. 623/17.16 |

FOREIGN PATENT DOCUMENTS

| | | |
|---|---|---|
| SU | 1 107 854 | 8/1984 |
| WO | WO 98/58604 | 12/1998 |

\* cited by examiner

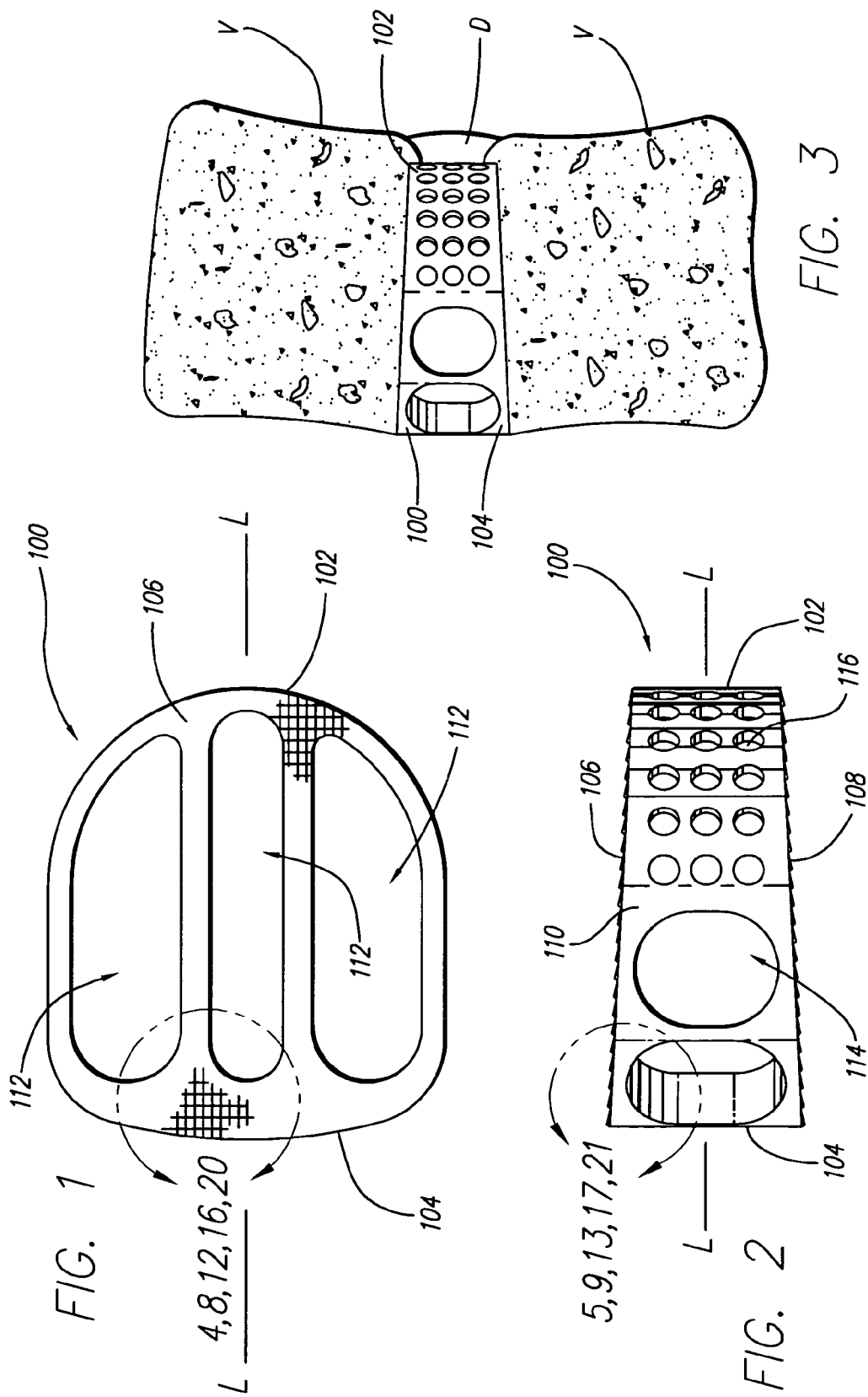

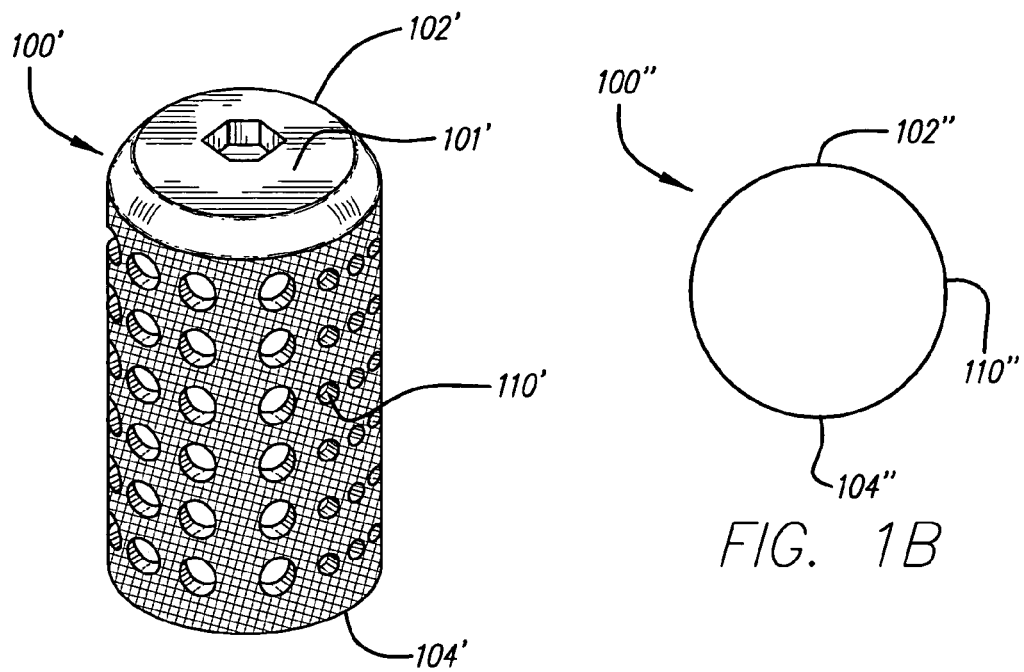
FIG. 1A
FIG. 1B
FIG. 1C
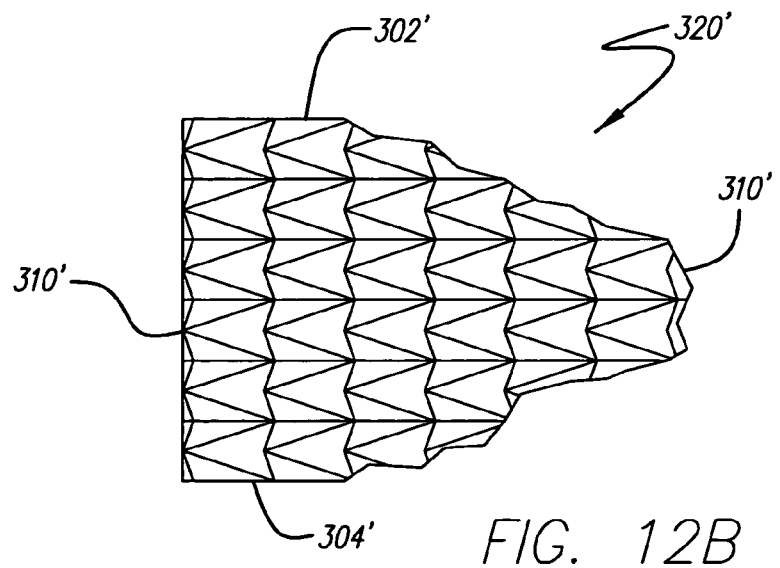
FIG. 12B

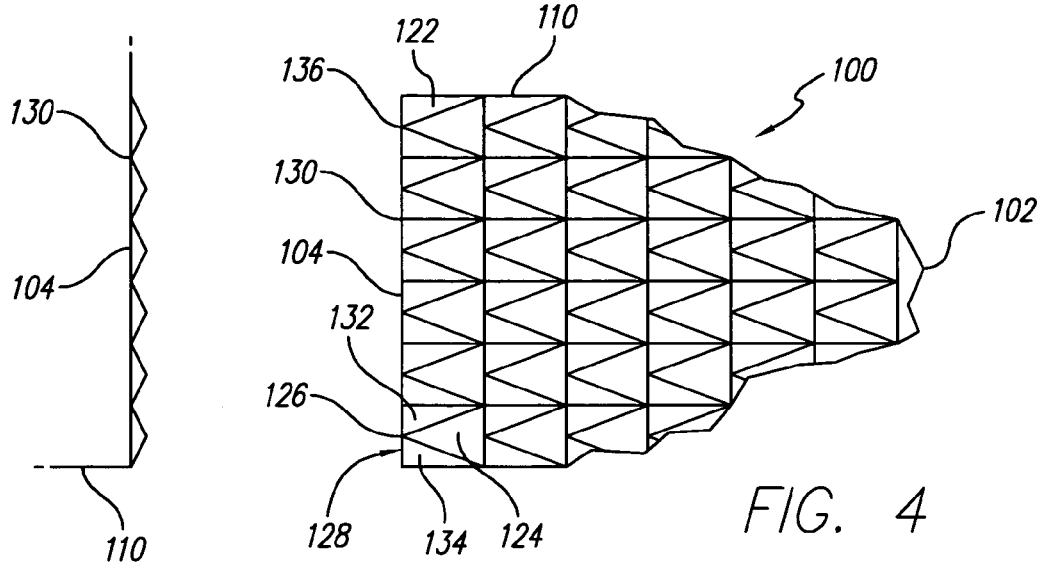
FIG. 6
FIG. 4
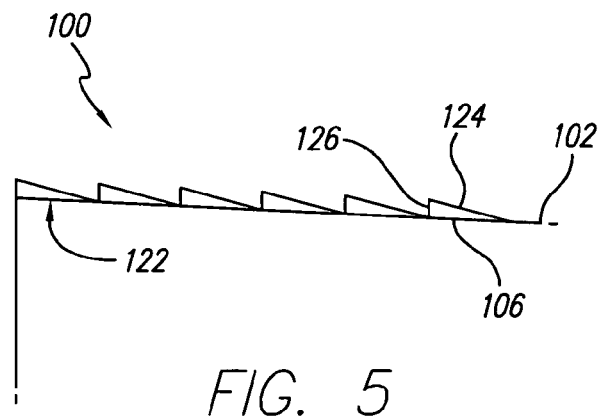
FIG. 5
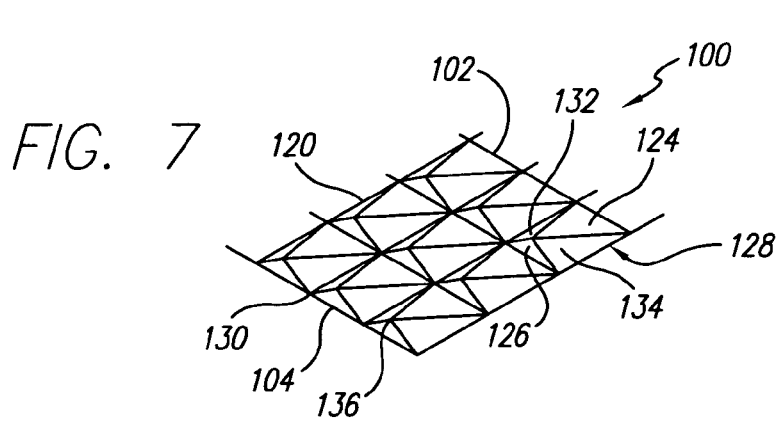
FIG. 7

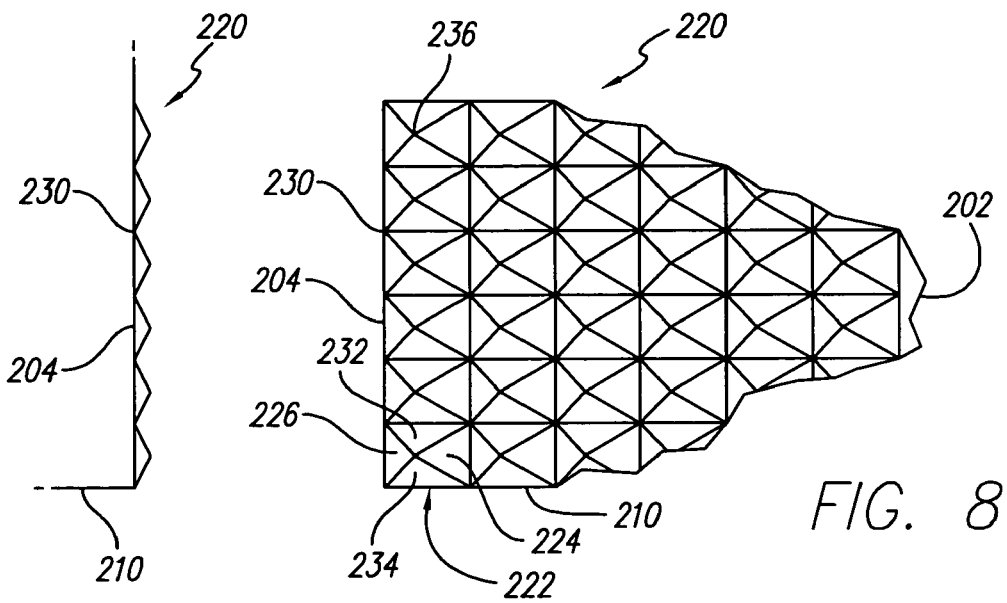
FIG. 10
FIG. 8
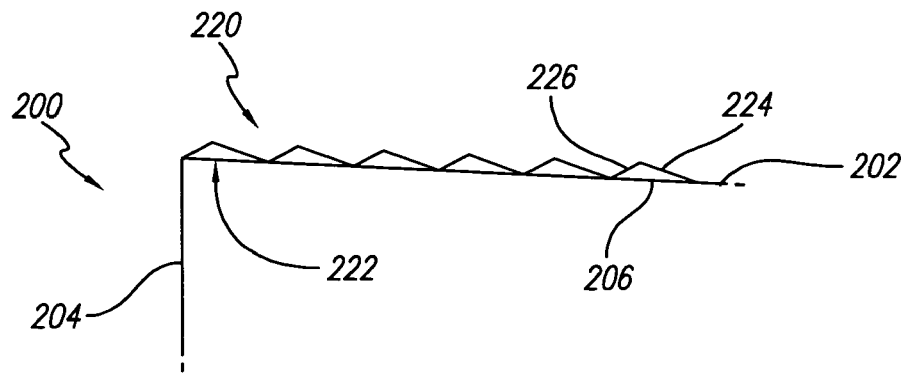
FIG. 9
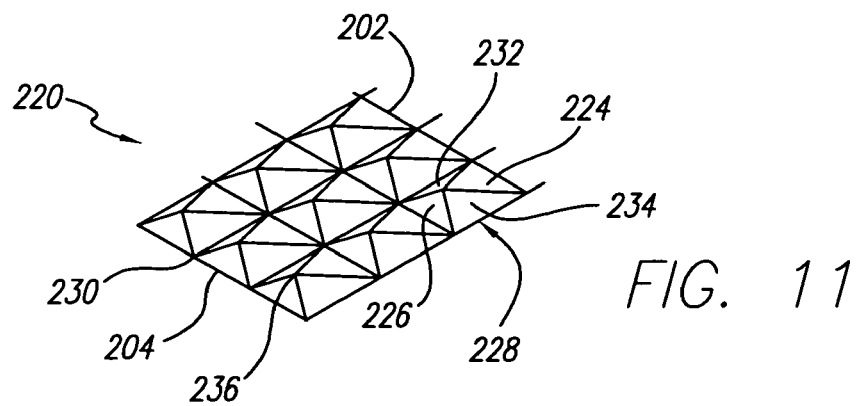
FIG. 11

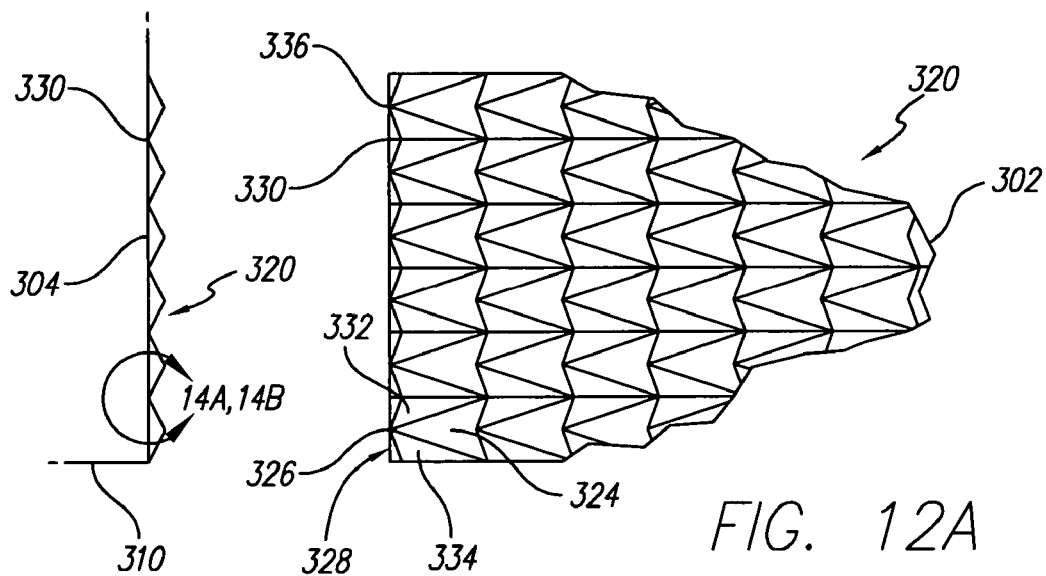
FIG. 12A
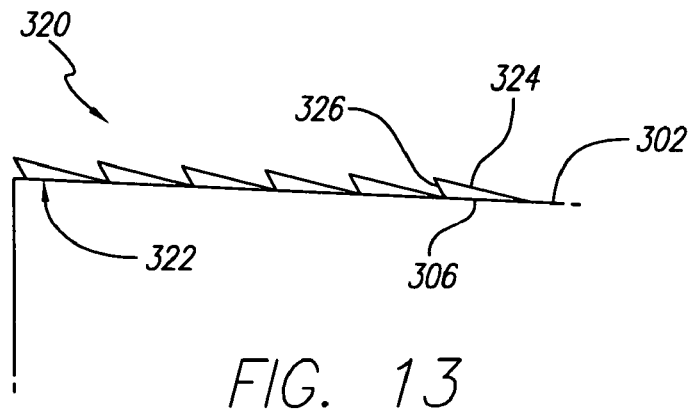
FIG. 14
FIG. 13
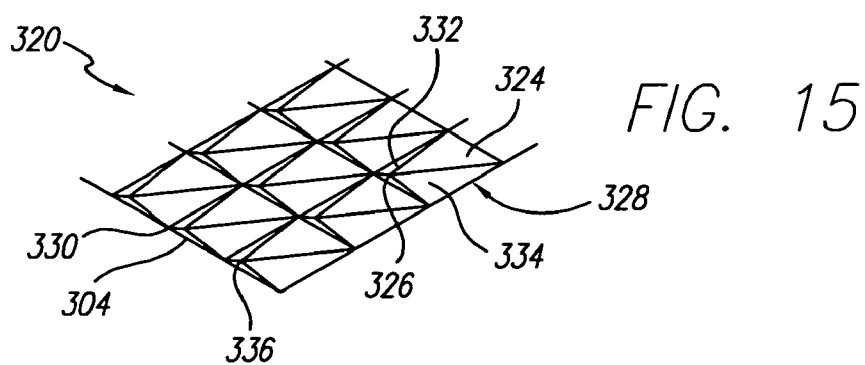
FIG. 15

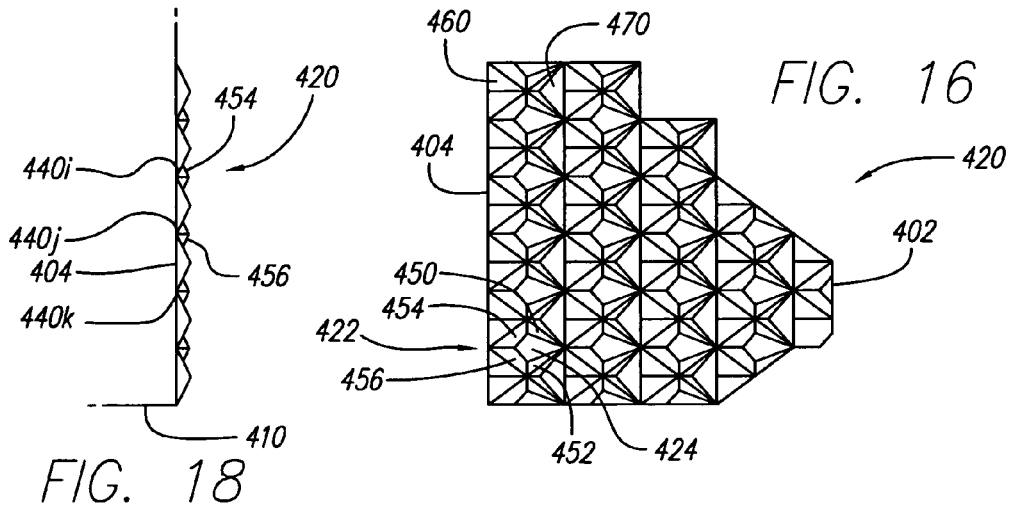
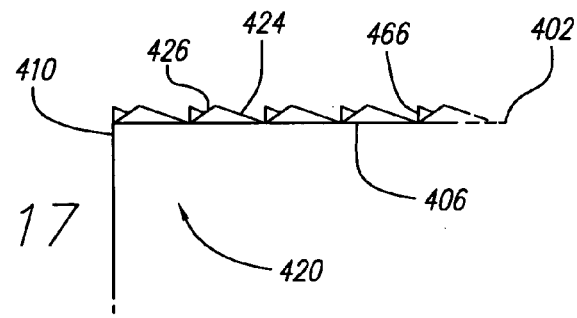
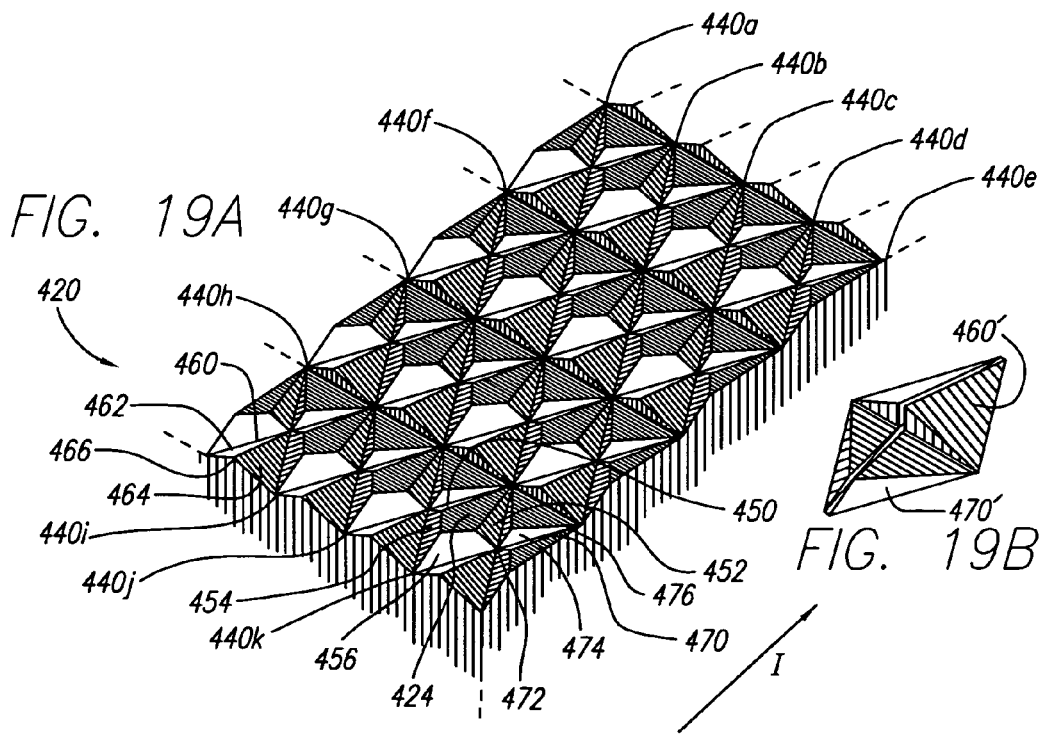

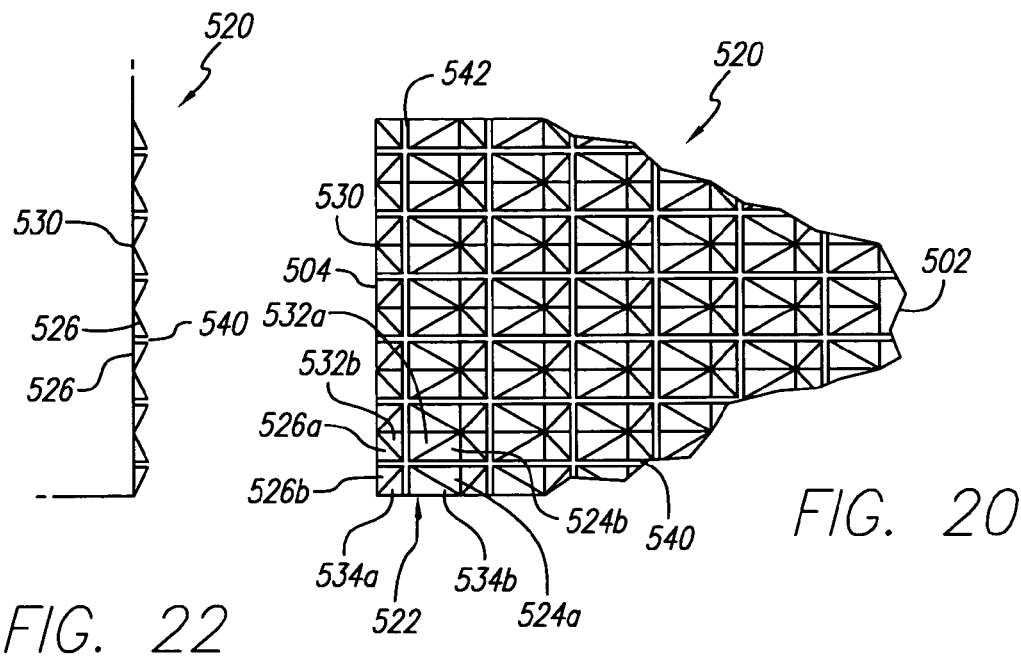
FIG. 22
FIG. 20
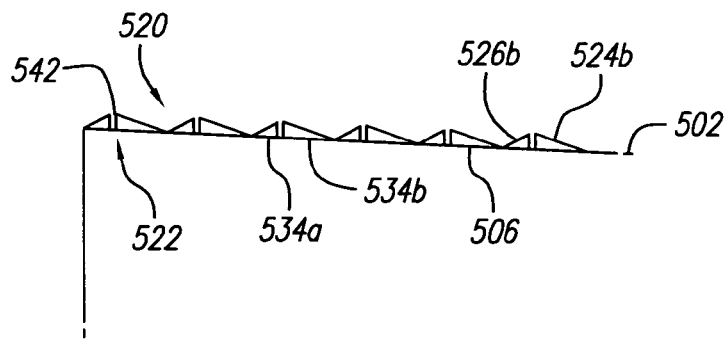
FIG. 21
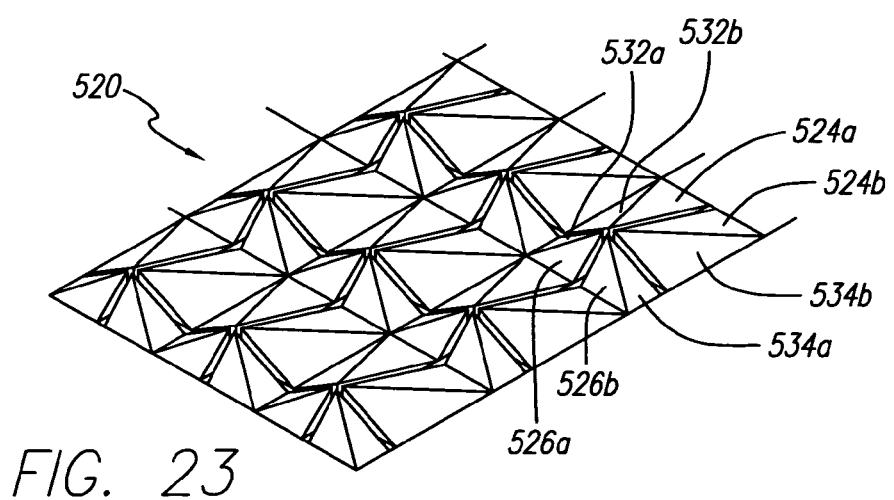
FIG. 23

SPINAL IMPLANT SURFACE CONFIGURATION WITH A PROJECTION HAVING A BACK CUT

This application is a continuation of application Ser. No. 09/457,228, filed Dec. 8, 1999, now U.S. Pat No. 6,827,740, which is incorporated herein by reference.

BACKGROUND OF THE INVENTION

Description Of The Related Art

The present invention relates to interbody spinal implants for placement between adjacent vertebral bodies of a human spine, and more specifically to a specialized surface for such interbody implants, for engaging the adjacent vertebral bodies. Vital to the functioning of all interbody spinal implants is their ability to remain properly located within the spine after installation. In U.S. Pat. Nos. 5,593,409 and 5,609,635, Michelson described the use of surface roughenings, such as knurling or ratcheting on the opposed upper and lower vertebral body engaging surfaces of interbody spinal fusion implants. Knurling has been particularly beneficial for increasing the grip of the implant surface to the adjacent vertebral bodies in a rather uniform manner without a directional bias. Spinal implants have a propensity to move in a particular direction, which is opposite to their path of insertion, because this is the path of least resistance. Such propensity to move is further increased when the opposed upper and lower vertebral body engaging surfaces are in angular relationship to each other, such that they are spaced further apart at the implant's trailing end than at the implant's leading end. In such circumstances where it is desirable then to gain stability in resistance to a particular direction of movement of the interbody spinal implant, the use of a plurality of forward facing ratchetings on the implant's vertebral body engaging surfaces has been preferable to the previously described knurling for that purpose.

The term "ratcheting" as used herein is defined as a plurality of angular teeth or ridges or protrusions projecting from the surface of an implant to resist motion of the implant at least in one direction. The phrase "forward facing ratchetings" as used herein is defined as a ratcheting having at least one forward facing facet having a length greater than a rearward facing facet and an angle from the implant surface from which the forward facing facet arises that is less steep than the angle of the rearward facet. On an implant surface, forward facing ratchetings facilitate the insertion of the implant in one direction and after insertion, resisting movement of the implant in a direction opposite to the direction of insertion. An example of forward facing ratchetings of the prior art is shown in partial fragmentary view in FIGS. 24A and 24B, generally referred to by the reference numeral 50.

Knurled surfaces of the related art provide some stability in all directions, but lack the ability to resist a particular direction of motion preferentially. The above-described ratcheted surface best resists motion in a particular direction. There exists a need for an improved interbody spinal implant surface configuration, wherein the opposed upper and lower vertebral body engaging surfaces of the implant are configured to be resistant to implant movement in all directions, and preferentially or in particularly in one direction.

SUMMARY OF THE INVENTION

The present invention relates to interbody spinal implants having a specialized surface configuration on the opposed exterior surfaces adapted for engaging the vertebral bodies adjacent a disc space into which the interbody implant is to be implanted. Such an implant surface configuration has utility with a wide variety of shapes of interbody spinal implants where enhanced skeletal fixation is desired. Such an implant surface configuration can provide for enhanced stability, increased surface area, and a surface for the delivery of fusion promoting substances other than bone. In a preferred embodiment, the implant surface can provide for resisting motion in all directions, and particularly in at least one direction, such as counter to the direction of insertion of the implant.

While various embodiments of the present invention are presented by way of example only and not limitation, common to each of them is that the surface configuration incorporates a plurality of spatially integrated surface projections having at least one forward facing facet directed at least in part toward the leading end of the implant and at least one rearward portion directed at least in part toward the opposite trailing end of the implant. By way of example and not limitation, the rearward portion may be a facet, a line, or an edge of the rearward aspect of the surface projection formed where two facets come together. Each of the forward and rearward facets have a length and a slope. The length of the forward facet is longer than the length of the rearward facet. The slope of the rearward facet is steeper than the slope of the forward facet. In various embodiments, the surface projections also have opposed side facets directed generally toward the sides of the implant. The side facets are located between the forward facet and rearward facet and may converge toward each other in a direction away from the base of the surface projections. The surface comprises multifaceted ratcheted projections that are organized in geometrically disposed fields or arrays which are at a minimum located on at least a portion of the opposed vertebral body engaging surfaces of the implant. From the teachings disclosed herein, it is appreciated that the surface projections can be geometrically arranged in a pattern wherein at least a portion of the projection is aligned along a longitudinal, horizontal, diagonal, or curved line. The upper and lower surfaces of the implant can be at least in part arcuate or planar and can converge along a portion or all of the length of the implant.

In various preferred embodiments of the present invention, the rearward facets of the surface projections can be perpendicular or at angles greater or less than 90 degrees to at least one of the upper or lower surfaces of the implant from which the projections arise. The opposed side facets of the surface projections can have at least a first portion in a plane at an angle to the longitudinal axis of the implant. The opposed side facets can intersect each other, and can converge to form a peak at the top of each of the surface projections. The peaks can be aligned along lines that are perpendicular, parallel, or diagonal to the longitudinal axis of the implant. The surface projections can be cleaved such as by longitudinal and/or horizontal cuts to increase the number of exposed sides of the projections and thus increase the available surface area to contact and engage the bone of the adjacent vertebral bodies and increase the number of recessed areas to contain fusion promoting substances. Alternatively, the peaks of each surface projection can be cleaved, truncated, or flattened at least in part.

The surface projections can include a left forward side facet and a right forward side facet directed toward the leading end and sides, respectively, of the implant. Similarly, the surface projections can include a left rearward side facet and a right rearward side facet directed toward the trailing end and sides, respectively, of the implant. The side facets of adjacent surface projections can be spaced apart to define a groove therebetween. A plurality of adjacent surface projections can be spaced apart to form a plurality of grooves that can be parallel or at an angle to the longitudinal axis of the implant, wherein the angle can be less than 90 degrees. The grooves can have a horizontal cross section that is a V-shape, U-shape, or a box-like shape, for example.

Sequential projections can be positioned on an implant wherein each surface projection has forward facing facets facing the same direction, such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface contour suitable for the intended use. The surface projections can be oriented relative to one another to form fields or arrays that further can be geometrically disposed relative to one another, preferably in a pattern wherein at least a portion of the projection is aligned along a longitudinal, horizontal, diagonal, or curved line.

The surface configuration of the present invention can be formed by casting, machining, or any other techniques known to one of ordinary skill in the art. The present surface configuration may readily be machined by milling the implant surface from side to side, across the upper and lower vertebral body engaging surfaces, to form ratchetings generally disposed perpendicular to the long axis of the implant and generally formed facing to the insertion end of the implant. The ratchetings may be cross machined with an angled cutting face to form grooves passing through the ratchetings. For example, a milling machine having a cutting tool, with a V-shaped profile, can be run through the plurality of ratchetings parallel to the longitudinal axis of the implant to form the above-described surface. In a preferred embodiment, the V-shaped cutting tool of the milling machine has opposed cutting faces with an angle of approximately 90 degrees to each other, which faces are each at a 45-degree angle to the plane of the surfaces being machined. Without departing from the scope of the present invention, the angle of the cutting faces can be more or less than 90 degrees, and the angle of the cutting face to be cut can be more or less than 45 degrees. It is appreciated that rather than the cutting element being run parallel to the longitudinal axis of the implant, the cutting element could be run at some other angle. By way of example only and not limitation, this angle could be at 45 degrees to the longitudinal axis of the implant and to the projections. Each surface projection could then be formed by a cutter crossing in two passes to form two grooves at a 90 degree angle to each other.

The surface of the present invention for engaging each of the adjacent vertebral bodies may be incorporated into various types of spinal implants. Such spinal implants may be for the purpose of achieving interbody spinal fusion, or for stabilizing a device to space apart and allow motion between the adjacent vertebral bodies. Such spinal implants may comprise any artificial or naturally occurring material appropriate for the intended purpose. Such materials would include, but are not limited to, implant quality metals, including, but not limited to, titanium and its alloys, surgical grade plastics and plastic composites which may or may not be bioresorbable, ceramics, and cortical bone. Some examples of interbody spinal implants that may benefit from the present teaching, include but are not limited to the following patents and applications by Michelson which are incorporated by reference herein: U.S. Pat. Nos. 5,015,247; 5,522,899; 5,593,409; 5,609,635; 5,860,973; and application Ser. No. 08/480,904.

BRIEF DESCRIPTION OF THE DRAWINGS

FIG. 1 is a top plan view of an interbody spinal implant having a surface configuration in accordance with the present invention.

FIG. 1A is a perspective view of an implant having arcuate surfaces and an end cap in accordance with an embodiment of the present invention.

FIG. 1B is a top elevational view of an implant having a leading end, a trailing end, and sides forming a circle in accordance with an embodiment of the present invention.

FIG. 1C is a graphical representation of a motion preserving device in accordance with an embodiment of the present invention.

FIG. 2 is a side elevation view of the spinal implant of FIG. 1.

FIG. 3 is a side elevation view of the interbody spinal implant of FIG. 1 installed in an implantation site formed across the disc space between two adjacent vertebral bodies of the spine shown in partial cross-section.

FIG. 4 is an enlarged fragmentary top plan view of an implant surface of one embodiment of the present invention from a view taken along area 4 of FIG. 1.

FIG. 5 is a fragmentary side elevation view of the implant surface of FIG. 4 from a view taken along area 5 of FIG. 2.

FIG. 6 is a fragmentary end elevation view of FIG. 4.

FIG. 7 is a fragmentary perspective view of the implant surface of FIG. 4.

FIG. 8 is an enlarged fragmentary top plan view of a second embodiment of the implant surface of the present invention from a view taken along area 8 of FIG. 1.

FIG. 9 is a fragmentary side elevation view of the implant surface of FIG. 8 from a view taken along area 9 of FIG. 2.

FIG. 10 is a fragmentary end view of the implant surface of FIG. 8.

FIG. 11 is a fragmentary perspective view of the implant surface of FIG. 8.

FIG. 12A is an enlarged fragmentary top plan view of a third embodiment of the implant surface of the present invention from a view taken along area 12 of FIG. 1.

FIG. 12B is an enlarged fragmentary top plan view of another embodiment of the implant surface of the present invention from a view taken along area 12 of FIG. 1.

FIG. 13 is a fragmentary side elevation view of the implant surface of FIG. 12A from a view taken along area 13 of FIG. 2.

FIG. 14 is a fragmentary end view of FIG. 12A.

FIG. 15 is a fragmentary perspective view of the implant surface of FIG. 12A.

FIG. 16 is an enlarged fragmentary top plan view of a fourth embodiment of the implant surface of the present invention from a view taken along area 16 of FIG. 1.

FIG. 17 is a fragmentary side elevation view of the implant surface of FIG. 16 from a view taken along area 17 of FIG. 2.

FIG. 18 is a fragmentary end view of FIG. 16.

FIG. 19A is an enlarged fragmentary perspective view of the implant surface of FIG. 16.

FIG. 19B is an enlarged fragmentary perspective view of a variation on the second and third surface projections of the fourth embodiment of the implant surface of the present invention with a cleave therethrough.

FIG. 20 is an enlarged fragmentary top plan view of a fifth embodiment of the implant surface of the present invention from a view taken along area 20 of FIG. 1.

FIG. 21 is a fragmentary side elevation view of the implant surface of FIG. 20 from a view taken along line 21 of FIG. 2.

FIG. 22 is a fragmentary end view of FIG. 20.

FIG. 23 is an enlarged fragmentary perspective view of the implant surface of FIG. 20.

DETAILED DESCRIPTION OF THE DRAWINGS

Figure 14A:
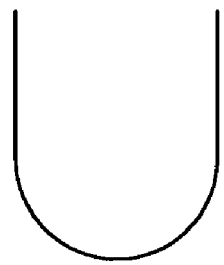
FIG. 14A is an enlarged fragmentary side view of a groove having a U-shape in accordance with an embodiment of the present invention from a view taken along area 14A of FIG. 14.

As shown in FIGS. 1-7, an interbody spinal implant 100 has a leading end 102, a trailing end 104, an upper surface 106, a lower surface 108, and a side wall 110 between upper and lower surfaces 106, 108. Upper and lower surfaces 106, 108 may converge from trailing end 104 to leading end 102 along a longitudinal axis L of implant 100 as shown, or may diverge, be parallel, or any combination thereof. Upper and lower surfaces 106, 108 are configured to be placed against and in contact or engagement with the bone of vertebral bodies V of two adjacent vertebrae adjacent disc D of the human spine. Upper and lower surfaces 106,108 and side wall 110 may include large and/or small openings 112, 114, and 116, respectively, to permit bone growth into and through implant 100. Upper and lower surfaces 106,108 of implant 100 can be generally planar as shown in the figures, or can be opposed arcuate surfaces as shown and described in U.S. Pat. No. 5,593,409, incorporated herein by reference, or any other configuration suitable for the desired use.

As shown in detail in FIGS. 4-7, at least a portion of upper and lower surfaces 106, 108 of implant 100 have a surface configuration generally referred to by the numeral 120. In accordance with a first embodiment of the present invention, surface configuration 120 includes surface projections 122 configured to facilitate insertion of implant 100 into an implantation site while resisting expulsion of implant 100 in a direction opposite to the direction of insertion. Each of surface projections 122 has an angled forward facet 124 directed at least in part toward leading end 102 of implant 100 and a rearward facet 126 directed at least in part toward trailing end 104 of implant 100. Forward facet 124 has a length greater than the length of rearward facet 126. Rearward facet 126 has a slope that is steeper than the slope of forward facet 124. In this embodiment, the base of rearward facet 126 forms an angle of approximately 90 degrees with respect to upper and/or lower surfaces 106, 108 of implant 100. It is appreciated that the angle of the base of rearward facet 126 with respect to upper and/or lower surfaces 106, 108 of implant 100 may be perpendicular to, greater than perpendicular to, or less than perpendicular to the base of the surface where the facet arises. Forward facet 124 forms an angle in the range of approximately 10 to 60 degrees, with 25-45 degrees being preferred, with respect to upper and/or lower surfaces 106, 108. Each one of surface projections 122 also has a left side facet 132 and a right side facet 134 directed toward the sides of implant 100.

In this embodiment of surface configuration 120, a plurality of surface projections 122 are spaced apart laterally (side to side) by longitudinal grooves 130 formed along the longitudinal axis L of implant 100. In one embodiment, longitudinal grooves 130 have a V-shaped horizontal cross-section. The lower most portions of left and right side facets 132, 134 of consecutive side-by-side projections 122 can be coincident with each other or may be spaced apart, any space therebetween can be at least in part flat, curved, sloped or otherwise configured. Each surface projection 122 has left and right side facets 132, 134 that converge to form a high point or peak 136 at the top of each surface projection 122. Each peak 136 can be aligned along lines that are perpendicular, parallel, and/or diagonally oriented to longitudinal axis L of implant 100. The left and right side facets 132, 134 resist side-to-side motion of implant 100 after it is inserted into the implantation space. Peaks 136 engage the bone of vertebral bodies V adjacent to implant 100 in the implantation site. It is appreciated that in a variation of the present invention, the peaks may be modified such as to be truncated or cut off to have a broader rather than sharper upper most surface. Moreover, the peaks can be cleaved in one or more directions so as to increase the surface area useful for engaging the bone of the vertebral bodies. The relieved areas of the cleaved projections are useful for containing and carrying fusion promoting substances other than bone such as bone morphogenetic proteins and genetic materials coding for the production of bone, or bone itself which could by way of example be in the form of a paste. It is further appreciated that for all the various embodiments of the surface configuration of the present invention, longitudinal grooves 130 can have horizontal cross-sections in a variety of configurations such as, without limitation, square-shaped or U-shaped configurations.

Sequential projections can be positioned on an implant wherein each surface projection has forward facing facets facing the same direction such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface configuration suitable for the intended use. The surface projections can be oriented relative to one another to form an array and are preferably geometrically disposed relative to one another in a pattern wherein at least a portion of the projection is aligned along a longitudinal, horizontal, diagonal, or curved line. Further, it is appreciated that the surface of the present invention can be useful with spinal implants of various configurations, including configurations wherein at least one of leading end, trailing end, and sides of the spinal implant is curved. By way of example and not limitation, the leading end, trailing end, and sides of the spinal implant can form an oval, an oblong, or a circle. As shown in FIGS. 8-11, a second embodiment of the surface configuration of the present invention is generally referred to by the numeral 220. Surface configuration 220 includes surface projections 222 to facilitate insertion of implant 100 into an implantation site while resisting expulsion of implant 100 in a direction opposite to the direction of insertion. Each of surface projections 222 has an angled forward facet 224 directed at least in part toward leading end 202 of implant 100 and a rearward facet 226 directed at least in part toward trailing end 204 of implant 100.

Forward facet 224 has a length greater than the length of rearward facet 226. Rearward facet 226 has a slope that is steeper than the slope of forward facet 224. In this embodiment, the base of rearward facet 226 forms an angle of approximately 45 degrees with respect to upper and/or lower surfaces 206, 208 of implant 100. Each one of surface projections 222 has a left side facet 232 and a right side facet 234 directed toward the sides of implant 100, and forward facet 224 and rearward facet 226.

In this embodiment of surface configuration 220, longitudinal grooves 230 have a V-shaped horizontal cross-section. The lower most portions of left and right side facets 232, 234 of consecutive side-by-side projections 222 can be coincident with each other or may be spaced apart, any space therebetween can be at least in part flat, curved, sloped or otherwise configured. Each surface projection has left and right side facets 232, 234 that converge to form a high point or peak 236 at the top of each surface projections 222. Each peak 236 can be aligned along lines that are perpendicular, parallel, and/or diagonally oriented to the longitudinal axis L of implant 100. The left and right side facets 232, 234 resist side-to-side motion of implant 100 after it is inserted into the implantation space. Peaks 236 engage the bone of the vertebral bodies adjacent to implant 100 in the implantation site.

Figure 14B:
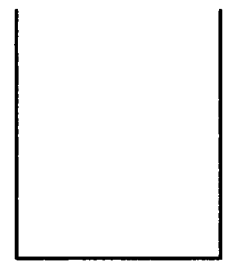
FIG. 14B is an enlarged fragmentary side view of a groove having a box-shape in accordance with an embodiment of the present invention from a view taken along area 14B of FIG. 14.
Figure 14C:
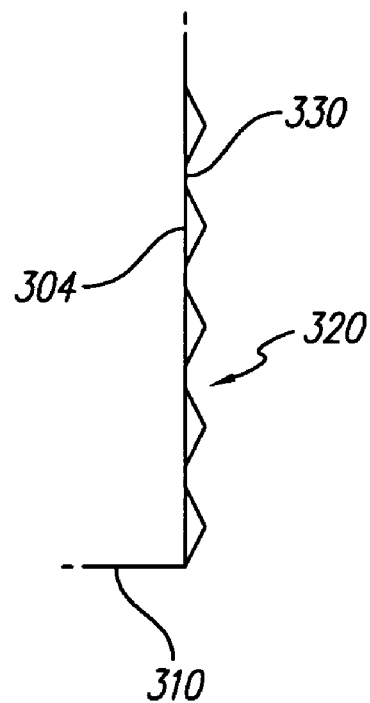
FIG. 14C is a fragmentary end view of a plurality of surface projections spaced apart from one another in accordance with an embodiment of the present invention.
Figure 24A:
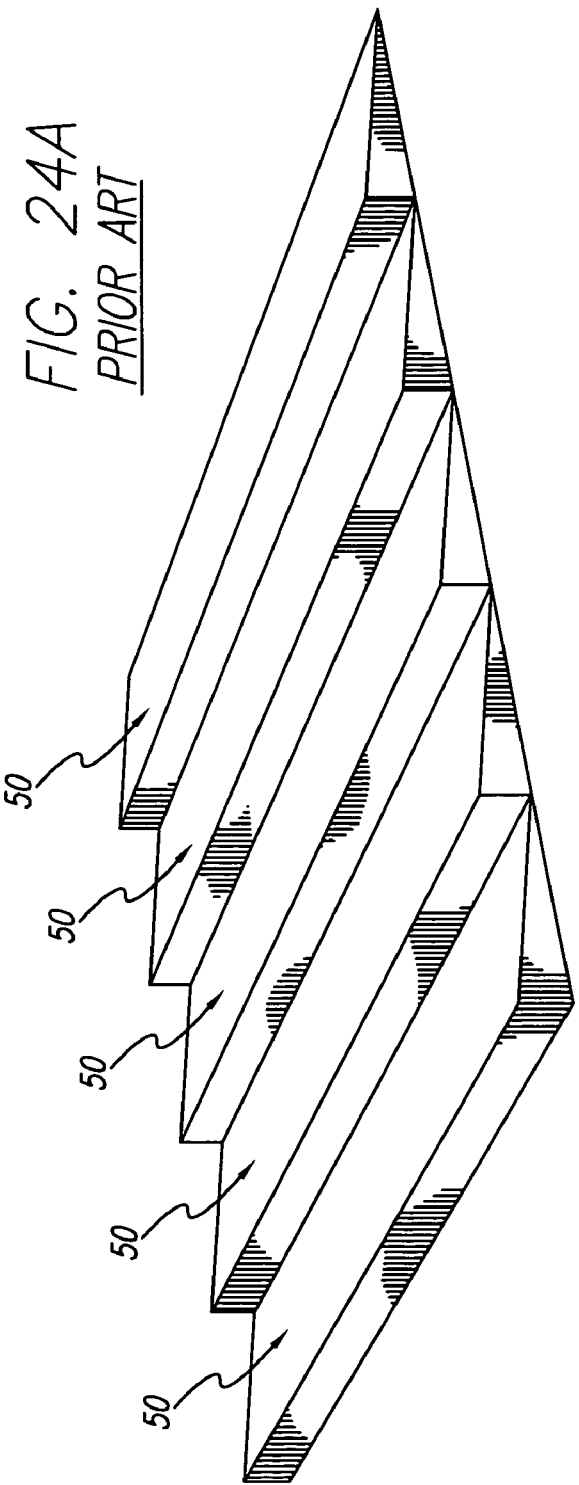
FIGS. 24A and 24B are perspective and side elevation views, respectively, of a prior art implant surface having forward facing ratchetings.
Figure 24B:
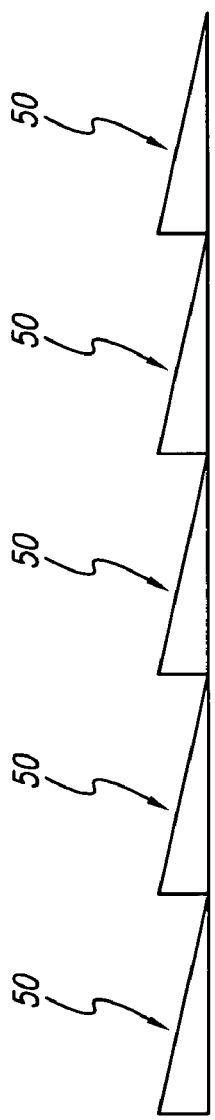

As shown in FIGS. 12-15, a third embodiment of the surface configuration of the present Invention is generally referred to by the numeral 320 is shown. Surface configuration 320 includes surface projections 322 to facilitate insertion of implant 100 into an implantation site while resisting expulsion of implant 100 in a direction opposite to the direction of insertion. Each of surface projections 322 has an angled forward facet 324 directed at least in part toward leading end 302 of implant 100 and a rearward facet 326 directed at least In part toward trailing end 304 of implant 100. Forward facet 324 has a length greater than the length of rearward facet 326. Rearward facet 326 has a slope that is steeper than the slope of forward facet 324. In this embodiment, the base of rearward facet 326 is "back cut" to form an angle greater than 90 degrees with respect to upper and/or lower surfaces 306, 308 of implant 100. The rearward facet 326 and the forward facet 324 have a negative direction of inclination, i.e., a negative slope, as shown in FIG. 13. The configuration of rearward facet 326 further enhances resistance of motion of the implant in a direction opposite to the direction of insertion. It is appreciated that the angle of the base of rearward facet 326 with respect to upper and/or lower surfaces 306, 308 of implant 100 can be any other angle suitable for the intended purpose of the present invention. Each one of surface projections 322 has a left side facet 332 and a right side facet 334 directed toward the sides of implant 100, and a forward facet 324 and a rearward facet 326.

In this embodiment of surface configuration 320, longitudinal grooves 330 have a V-shaped horizontal cross section. The lower most portions of left and right side facets 332, 334 of consecutive side-by-side projections 322 can be coincident with each other or may be spaced apart, and any space therebetween can be at least in part flat, curved, sloped or otherwise configured. Each surface projection 322 has left and right side facets 332, 334 that converge to form a high point or peak 336 at the top of each surface projection 322. Each peak 336 can be aligned along lines that are perpendicular, parallel, and/or diagonally oriented to the longitudinal axis L of implant 100. The left and right side facets 332, 334 resist side-to-side motion of implant 100 after it is inserted into the implantation space. Peaks 336 engage the bone of vertebral bodies V adjacent to implant 100 in the implantation site.

As shown in FIGS. 16-19B, a fourth embodiment of the surface configuration of the present invention is generally referred to by the numeral 420. Surface configuration 420 includes surface projections 422 configured to facilitate insertion of implant 100 in the direction of insertion into an implantation site while resisting expulsion of implant 100 in a direction opposite to the direction of insertion. Each of surface projections 422 has an angled forward facet 424 directed toward leading end 402 of implant 100 and a rearward portion 426 directed toward trailing end 404 of implant 100. Forward facet 424 has a length greater than the length of rearward portion 426. Rearward portion 426 has a slope that is steeper than the slope of forward facet 424. In this embodiment, the base of rearward portion 426 forms an angle of approximately 90 degrees with respect to upper and/or lower surfaces 406, 408 of implant 100. Rearward portion 426 can be a portion of surface projection 422, such as a facet, an edge, or a line for example. Each one of surface projections 422 has a left side forward facet 450, a right side forward facet 452, a left side rearward facet 454, and a right side rearward facet 456 directed toward the front and sides, and directed toward the rear and sides of implant 100, respectively, and forward facet 424 and rearward portion 426.

Surface configuration 420 can further include a second plurality of surface projections 460 having at least a left forward side facet 462 and a right forward side facet 464 directed at least in part toward leading end 402 and sides of implant 100, respectively, and at least one rearward facet 466 directed at least in part toward trailing end 400. Left and right forward side facets 462, 464 have at least a first portion in a plane at an angle to the longitudinal axis of implant 100. Second surface projections 460 can be interspersed with surface projections 422.

Surface configuration 420 can further comprise a third plurality of surface projections 470 having at least a left rearward side facet 472 and a right rearward side facet 474 directed at least in part toward trailing end 404 and sides of implant 100, respectively, and at least one forward facet 476 directed at least in part toward leading end 402. Left and right rearward side facets 472, 474 have at least a first portion in a plane at an angle to the longitudinal axis of implant 100. Third surface projections 470 can be interspersed with surface projections 422 and/or second surface projections 460. Surface projections 422 may have a length approximating the combined length of second surface projections 460 and third surface projections 470.

In this embodiment, surface configuration 420 has angled grooves 440a-k that form a plurality of surface projections 422. In this example, angled grooves 440a-k are formed at an angle that is approximately 45 degrees to longitudinal axis L of spinal implant 100 and in this example, angled grooves 440a-k are approximately 90 degrees to one another. The angled grooves 440a-k can be formed, if machined, by first passing a cutting element at a 45 degree angle to the longitudinal axis L of implant 100 and then passing the cutting element at a 90 degree angle to the path of the first pass of the cutting element, or otherwise formed by casting, molding, and other methods for forming a surface configuration. It is appreciated that angled grooves 400a-k can be formed at various angles to the longitudinal axis L of implant 100 and to each other. For example, such angles can be less than 180 degrees.

In this embodiment of surface configuration 420, angled grooves 440a-k have a V-shaped horizontal cross-section. Each surface projection 422 has left and right side facets 432 and 434 that are convergent and form a high point or peak 436 at the top of each surface projections 422. Each peak 436 can be aligned along lines that are horizontally, longitudinally, and/or diagonally oriented along implant 100. The left and right side forward and rearward facets 450, 452, 454, 456 function to prevent side-to-side motion of implant 100 after it is inserted into the implantation space. Peaks 436 may also function like teeth to engage the bone of vertebral bodies V adjacent to the implant in the implantation site.

FIG. 19B shows a variation of second and third surface projections 460', 470' that can be cleaved in one or more directions to increase the number of exposed sides of each projection and thus increase the surface area of the implant bone engaging surface available to contact the bone of the vertebral bodies. A preferred embodiment of this variation of the second and third surface projections 460', 470' are cleaved by a longitudinal groove.

As shown in FIGS. 20-23, a fifth embodiment of the surface configuration of the present invention is generally referred to by the numeral 520. Surface configuration 520 includes surface projections 522 to facilitate insertion of implant 100 into an implantation site while resisting expulsion of implant 100 in a direction opposite to the direction of insertion. Surface projections 522 can be cleaved in one or more directions to increase the number of exposed sides of each projection and thus increase the surface area of the implant bone engaging surface available to contact the bone of the vertebral bodies. For example, the surface projections can be cleaved by a longitudinal cut 540 generally parallel to the longitudinal axis L of implant 100 to form a surface projection having nine exposed sides. The surface projections may further be cleaved by a horizontal cut 542 generally perpendicular to the longitudinal axis L of implant 100 to form a surface projection having eighteen exposed sides. The cuts can penetrate the surface projection at a depth substantially equal to that of the height of the surface projections as measured from the upper or lower surfaces of the implant. The cuts can be oriented along at least one of the longitudinal axis of the implant, an axis perpendicular to the longitudinal axis of said implant, and an axis at an angle between the longitudinal axis and the axis perpendicular to the longitudinal axis of the implant. It is appreciated that cuts 540 and 542 may be formed as part of the molding process for forming the surface projections.

When cleaved by longitudinal cut 540 and horizontal cut 542, each of surface projections 522 has angled forward facet 524a, 524b directed at least in part toward leading end 502 of implant 100 and rearward facets 526a, 526b directed at least in part toward trailing end 504 of implant 100. Forward facet 524 has a length greater than the length of rearward facet 526. Rearward facets 526a, 526b have a slope that is steeper than the slope of forward facets 524a, 524b. The cleaved portion of surface projection 522 can be spaced apart by a predetermined distance and the space can be at least in part flat, curved, or any other surface configuration suitable for the intended use. In this embodiment, the base of rearward facets 526a, 526b forms an angle of approximately 45 degrees with respect to upper and/or lower surfaces 506, 508 of implant 100. Each one of surface projections 522 has left side facets 532a, 532b and right side facets 534a, 534b directed toward the sides of implant 100, and forward facets 524a, 524b and rearward facet 526a, 526b. In this embodiment of surface configuration 520, longitudinal grooves 530 have a V-shaped horizontal cross-section and each surface projection 522 has left and right side facets 532a, 532b, 534a, 534b that converge toward one another. The left and right side facets 532a, 532b, 534a, 534b resist side-to-side motion of implant 100 after it is inserted into the implantation space. The surface configuration of the present invention can be formed by molding, machining or otherwise. A preferred surface configuration of the present invention may readily be machined by milling from side to side, across the upper and lower vertebral body engaging surfaces, surface projections. A milling machine with a cutting tool having an angled cutting face such as a V-shaped profile can then be run through the plurality of surface projections parallel to the longitudinal axis of the implant to form the above-described surface. In a preferred embodiment, the V-shaped cutting tool of the milling machine has faces with an angle of approximately 90 degrees, which faces are at a 45-degree angle to the plane of the surfaces being so machined. Without departing from the present invention, the angle of the cutting faces can be more or less than 90 degrees, the angle of the cutting face to the surface to be cut can be more or less than 45 degrees, and rather than running the cutter element parallel to the longitudinal axis of the implant, the cutting element may be run at an angle. By way of example only and not limitation, this angle may be at 45 degrees to the longitudinal axis of the implant and each surface projection can be formed by two grooves crossing the projections at a 90 degree angle to each other.

The spinal implants of the present invention are made of artificial or naturally occurring materials suitable for implantation in the human spine. The implants can comprise bone including, but not limited to, cortical bone, materials other than bone, such as metals including, but not limited to, titanium and its alloys or ASTM material, surgical grade plastics, plastic composites, ceramics, or other materials suitable for use as a spinal implant. The implants of the present invention can further comprise or be combined with bone growth promoting materials, including but not limited to, bone, bone morphogenetic proteins, hydroxyapatite, and genes coding for the production of bone. The implants can be treated with a bone growth promoting substance, can be a source of osteogenesis, or can be bioabsorbable at least in part. The implants of the present invention can be formed of a porous material.

The spinal implants of the present invention can be for the purpose of achieving fusion. The upper and lower surfaces of the fusion implants can include at least one opening, each in communication with the other, to permit for the growth of bone from vertebral body to adjacent vertebral body through the implant. The implant can have an internal chamber and may also have an access opening for accessing the internal chamber, in which case the implant can further have a cover such as a cap 101' (shown in FIG. 1A) to close the access opening at least in part. Openings in the upper and lower surfaces of the implant can communicate with the internal chamber to permit further growth of bone from vertebral body to adjacent vertebral body through the implant. The internal chamber can contain bone growth promoting materials, including but not limited to, bone, bone morphogenetic proteins, hydroxyapatite, and genes coding for the production of bone. The implants of the present invention can be formed of a material that intrinsically participates in the growth of bone from one of the adjacent vertebral bodies to the other of the adjacent vertebral bodies.

While various embodiments of the present invention are presented by way of example only and not limitation, common to each of them, is that the configuration of the surface is based on a plurality of surface projections disposed in arrays, each surface projection comprising at least one leading facet and at least one opposing trailing facet, in which the leading facet has a length greater than the trailing facet and the trailing facet has a steeper slope than the slope of the leading facet. The surface configuration is located on at least a portion of one of the opposed vertebral body engaging surfaces of the spinal implant.

While the implant shown in FIGS. 1, 2, and 3 is an interbody spinal fusion implant, it is appreciated that the surface configuration of the present invention is applicable to any interbody spinal fusion implants, including but not limited to, an artificial disc or motion preserving device having opposed surfaces incorporating the present inventive teachings for engaging each of the adjacent vertebral bodies.

It is believed that the operation and construction of the present invention will be apparent from the foregoing description and, while the invention shown and described herein has been characterized as particular embodiments, changes and modifications may be made therein without departing from the spirit and scope of the invention as defined in the following claims.

What is claimed is:

1. An interbody spinal implant for insertion between adjacent vertebral bodies of a human spine, said implant comprising:
   a leading end for introduction of said spinal implant into the spine, an opposite trailing end, spaced apart sides therebetween, and a mid-longitudinal axis passing through said leading and trailing ends;
   opposite upper and lower surfaces between said leading and trailing ends and said spaced apart sides, said upper surface adapted for placement in engagement with the bone of one of the vertebral bodies and said opposite lower surface adapted for placement in engagement with the bone of the other of the vertebral bodies when said implant is placed between the adjacent vertebral bodies; and
   a plurality of surface projections formed on said upper and lower surfaces of said implant, at least a first and a second of said surface projections each having a maximum height, at least one of said surface projections having a top, a forward facet directed at least in part toward the leading end, a rearward facet directed at least in part toward the trailing end, and opposed side facets converging toward one another between said forward facet and said rearward facet to intersect each other and form a peak at the top of said at least one of said surface projections, said peak of said at least one of said surface projections overlying at least a portion of another of said surface projections, said forward facet and said rearward facet having a length and a slope, the length of said forward facet being longer than the length of said rearward facet, said forward facet and said rearward facet both declining from said maximum height, in a direction toward said leading end, said forward facet having converging sides and a maximum width between said converging sides, said maximum width of said forward facet being greater than said maximum height of said at least one of said surface projections.

2. An interbody spinal implant for insertion between adjacent vertebral bodies of a human spine, said implant comprising:
   a leading end for introduction of said spinal implant into the spine, an opposite trailing end, spaced apart sides therebetween, and a mid-longitudinal axis passing through said leading and trailing ends;
   opposite upper and lower surfaces between said leading and trailing ends and said spaced apart sides, said upper surface adapted for placement in engagement with the bone of one of the vertebral bodies and said opposite lower surface adapted for placement in engagement with the bone of the other of the vertebral bodies when said implant is placed between the adjacent vertebral bodies; and
   a plurality of surface projections formed on said upper and lower surfaces of said implant, said surface projections including adjacent surface projections spaced apart to form a plurality of grooves therebetween, at least one of said grooves having a horizontal cross-sectional shape that is one of a v-shape, u-shape, and a box-like shape, at least a first and a second of said surface projections each having a maximum height, at least one of said surface projections having a forward facet directed at least in part toward the leading end, a rearward facet directed at least in part toward the trailing end, and opposed side facets directed generally toward said spaced apart sides of said implant, respectively, said side facets converging toward One another between said forward facet and said rearward facet in a direction away from one of said upper and lower surfaces of said implant said forward facet and said rearward facet having a length and a slope, the length of said forward facet being longer than the length of said rearward facet, said forward facet and said rearward facet both declining from said maximum height in a direction toward said leading end, said forward facet having converging sides and a maximum width between said converging sides, said maximum width of said forward facet being greater than said maximum height of said at least one of said surface projections.

3. An interbody spinal implant for insertion between adjacent vertebral bodies of a human spine, said implant comprising:
   a leading end for introduction of said spinal implant into the spine, an opposite trailing end spaced apart sides therebetween, and a mid-longitudinal axis passing through said leading and trailing ends;
   opposite upper and lower surfaces between said leading and trailing ends and said spaced apart sides, said upper surface adapted for placement in engagement with the bone of one of the vertebral bodies and said opposite lower surface adapted for placement in engagement with the bone of the other of the vertebral bodies when said implant is placed between the adjacent vertebral bodies; and
   a plurality of surface projections formed on said upper and lower surfaces of said implant, at least a first and a second of said surface projections each having at least one forward facing facet directed at least in part toward said leading end, at least one rearward facet directed at least in part toward said trailing end, and opposed side facets converging toward one another between said forward facet and said rearward facet, each of said forward facet and rearward facet having a length and a slope, the length of said forward facet being longer than the length of said rearward facet, the slope of said rearward facet being steeper than the slope of said forward facet; said first and second surface projections each having a base and a portion above said base, said portion above the base of said first and second surface projections extending outside of the perimeter of the base of a respective one of said first and second surface projections, said forward facet having converging sides and a maximum width between said converging sides, said base of said first surface projection and said base of said second surface projection being spaced apart by a distance as measured along a line transverse to the mid-longitudinal axis of said implant, the distance being less than said maximum width of said forward facet.

4. The spinal implant of claim 1, wherein one of said facets is formed in the shape of a triangle having a vertex with an included angle greater than 90 degrees.

5. The spinal implant of claim 1, wherein the slope of said rearward facet is steeper than the slope of said forward facet.

6. The spinal implant of claim 1, wherein said rearward facet is at an angle to at least one of said upper and lower surfaces of said implant.

7. The spinal implant of claim 6, wherein said angle is greater than 90 degrees.

8. The spinal implant of claim 1, wherein said surface projections are oriented relative to one another to form an array.

9. The spinal implant of claim 1, wherein said upper and lower surfaces of said implant are at least in part arcuate.

10. The spinal implant of claim 1, wherein at least one of said leading end, trailing end, and sides are curved.

11. The spinal implant of claim 1, wherein said sides are curved.

12. The spinal implant of claim 1, wherein each of said leading end, trailing end, and sides are curved.

13. The spinal implant of claim 12, wherein said leading end, trailing end, and sides form a circle.

14. The spinal implant of claim 1, wherein said upper and lower surfaces of said implant are at least in part planar.

15. The spinal implant of claim 1, wherein said upper and lower surfaces converge toward each other along at least a portion of the length of said implant.

16. The spinal implant of claim 1, wherein said implant comprises a material other than bone.

17. The spinal implant of claim 1, wherein said implant comprises bone.

18. The spinal implant of claim 17, wherein said bone includes cortical bone.

19. The spinal implant of claim 1, wherein said implant comprises bone growth promoting material.

20. The spinal implant of claim 19, wherein said bone growth promoting material is one of bone morphogenetic protein, hydroxyapatite, and genes coding for the production of bone.

21. The spinal implant of claim 1, wherein said implant is treated with a bone growth promoting substance.

22. The spinal implant of claim 1, wherein said implant is a source of osteogenesis.

23. The spinal implant of claim 1, wherein said implant is at least in part bioabsorbable.

24. The spinal implant of claim 1, wherein said implant comprises metal.

25. The spinal implant of claim 24, wherein said metal includes titanium.

26. The spinal implant of claim 1, wherein said implant comprises at least one of a plastic material, a ceramic material, and a porous material.

27. The spinal implant of claim 1, wherein said implant is formed of a material that intrinsically participates in the growth of bone from one of the adjacent vertebral bodies to the other of the adjacent vertebral bodies.

28. The spinal implant of claim 1, wherein said implant is a motion preserving device adapted to space apart and allow motion between the adjacent vertebral bodies.

29. The spinal implant of claim 1, wherein said spinal implant is a fusion implant.

30. The spinal implant of claim 29, wherein said upper and lower surfaces include at least one opening to permit bone growth from adjacent vertebral body to adjacent vertebral body through said implant.

31. The spinal implant of claim 29, wherein said implant has an internal chamber and an access opening for accessing said internal chamber.

32. The spinal implant of claim 31, wherein said implant has a cap for closing said access opening.

33. The: spinal implant of claim 31, wherein said upper and lower surfaces include at least one opening in communication with said internal chamber to permit bone growth from adjacent vertebral body to adjacent vertebral body through said implant.

34. The spinal implant of claim 31, wherein said internal chamber is capable of containing bone growth promoting material.

35. The spinal implant of claim 34, further comprising said bone growth promoting material, said bone growth promoting material being one of bone morphogenetic protein, hydroxyapatite, and genes coding for the production of bone.

36. The spinal implant of claim 1, further comprising at least one opening capable of retaining fusion promoting materials.

37. The spinal implant of claim 1, in combination with a fusion promoting substance.

38. The spinal implant of claim 37, wherein said fusion promoting substance includes at least one of bone, bone morphogenetic protein, hydroxyapatite, and genes coding for the production of bone.

39. The spinal implant of claim 1, wherein each of said surface projections have a base, at least two of said bases being adjacent to one another.

40. The spinal implant of claim 1, wherein each of said surface projections have a base, at least two of said bases being spaced apart from one another along a direction generally parallel to the mid-longitudinal axis of said implant.

41. The spinal implant of claim 1, wherein each of said surface projections have a base, at least two of said bases being spaced apart from one another along a direction generally transverse to the mid-longitudinal axis of said implant.

42. The spinal implant of claim 1, wherein another of said surface projections has a forward facet, said forward facets of said surface projections facing the same direction.

43. The spinal implant of claim 1, wherein said peaks of at least two of said surface projections are aligned along lines that are at least one of perpendicular, parallel, and diagonal to the mid-longitudinal axis of said implant.

44. The spinal implant of claim 1, wherein said peaks of at least two of said surface projections are at the same height above one of said upper and lower surfaces of said implant.

45. The spinal implant of claim 1, wherein adjacent side facets of adjacent surface projections are spaced apart to define a groove therebetween.

46. The spinal implant of claim 1, wherein a plurality of adjacent surface projections are spaced apart to form a plurality of grooves therebetween.

47. The spinal implant of claim 46, wherein at least one of said grooves is parallel to the mid-longitudinal axis of said implant.

48. The spinal implant of claim 46, wherein at least two of said grooves cross each other.

49. The spinal implant of claim 3, wherein said rearward facet is at an angle to at least one of said upper and lower surfaces of said implant.

50. The spinal implant of claim 49, wherein said angle is greater than 90 degrees.

51. The spinal implant of claim 3, wherein said surface projections are oriented relative to one another to form an array.

52. The spinal implant of claim 3, wherein said upper and lower surfaces of said implant are at least in part arcuate.

53. The spinal implant of claim 3, wherein at, least one of said leading end, trailing end, and sides are curved.

54. The spinal implant of claim 3, wherein said sides are curved.

55. The spinal implant of claim 3, wherein each of said leading end, trailing end, and sides are curved.

56. The spinal implant of claim 55, wherein said leading end, trailing end, and sides form a circle.

57. The spinal implant of claim 3, wherein said upper and lower surfaces of said implant are at least in part planar.

58. The spinal implant of claim 3, wherein said upper and lower surfaces converge toward each other along at least a portion of the length of said implant.

59. The spinal implant of claim 3, wherein said implant comprises a material other than bone.

60. The spinal implant of claim 3, wherein said implant comprises bone.

61. The spinal implant of claim 60, wherein said bone includes cortical bone.

62. The spinal implant of claim 3, wherein said implant comprises bone growth promoting material.

63. The spinal implant of claim 62, wherein said bone growth promoting material is one of bone morphogenetic protein, hydroxyapatite, and genes coding for the production of bone.

64. The spinal implant of claim 3, wherein said implant is treated with a bone growth promoting substance.

65. The spinal implant of claim 3, wherein said implant is a source of osteogenesis.

66. The spinal implant of claim 3, wherein said implant is at least in part bioabsorbable.

67. The spinal implant of claim 3, wherein said implant comprises metal.

68. The spinal implant of claim 67, wherein said metal includes titanium.

69. The spinal implant of claim 3, wherein said implant comprises at least one of a plastic material, a ceramic material, and a porous material.

70. The spinal implant of claim 3, wherein said implant is formed of a material that intrinsically participates in the growth of bone from one of the adjacent vertebral bodies to the other of the adjacent vertebral bodies.

71. The spinal implant of claim 3, wherein said implant is a motion preserving device adapted to space apart and allow motion between the adjacent vertebral bodies.

72. The spinal implant of claim 3, wherein said spinal implant is a fusion implant.

73. The spinal implant of claim 72, wherein said upper and lower surfaces include at least one opening to permit bone growth from adjacent vertebral body to adjacent vertebral body through said implant.

74. The spinal implant of claim 72, wherein said implant has an internal chamber and an access opening for accessing said internal chamber.

75. The spinal implant of claim 74, wherein said implant has a cap for closing said access opening.

76. The spinal implant of claim 74, wherein said upper and lower surfaces include at least one opening in communication with said internal chamber to permit bone growth from adjacent vertebral body to adjacent vertebral body through said implant.

77. The spinal implant of claim 74, wherein said internal chamber is capable of containing .bone growth promoting material.

78. The spinal implant of claim 77, further comprising said bone growth promoting material, said bone growth promoting material being one of bone morphogenetic protein, hydroxyapatite, and genes coding for the production of bone.

79. The spinal implant of claim 3, further comprising at, least one opening capable of retaining fusion promoting materials.

80. The spinal implant of claim 3, in combination with a fusion promoting substance.

81. The spinal implant of claim 80, wherein said fusion promoting substance includes at least one of bone, bone morphogenetic protein, hydroxyapatite, and genes coding for the production of bone.

82. The spinal implant of claim 3, wherein said base of said first surface projection and said base of said second surface projection are adjacent to one another.

83. The spinal implant of claim 3, wherein said base of said first surface projection and said base of said second surface projection are spaced apart from one another along a direction generally parallel to the mid-longitudinal axis of said implant.

84. The spinal implant of claim 3, wherein said base of said first surface projection and said base of said second surface projection are along a line generally transverse to the mid-longitudinal axis of said implant.

85. The spinal implant of claim 3, wherein said forward facets of each of said first and second surface projections face the same direction.

86. The spinal implant of claim 3, wherein said opposed side facets are directed generally toward said spaced apart sides of said implant, respectively, said side facets converging toward each other in a direction away from one of said upper and lower surfaces of said implant.

87. The spinal implant of claim 3, wherein said opposed side facets intersect each other.

88. The spinal implant of claim 87, wherein said opposed side facets converge to form a peak at the top of said surface projection.

89. The spinal implant of claim 88, wherein said peaks of at least two of said surface projections are aligned along lines that are at least one of perpendicular, parallel, and diagonal to the mid-longitudinal axis of said implant.

90. The spinal implant of claim 88, wherein said peak of said first surface projection overlies at least a portion of said second surface projection.

91. The spinal implant of claim 88, wherein said peaks of said first and second surface projections are at the same height above one of said upper and lower surfaces of said implant.

92. The spinal implant of claim 86, wherein adjacent side facets of adjacent surface projections are spaced apart to define a groove therebetween.

93. The spinal implant of claim 86, wherein a plurality of adjacent surface projections are spaced apart to form a plurality of grooves therebetween.

94. The spinal implant of claim 93, wherein at least one of said grooves is parallel to the mid-longitudinal axis of said implant.

95. The spinal implant of claim 93, wherein at least two of said grooves cross each other.

96. The spinal implant of claim 93, wherein at least one of said grooves has a horizontal cross-sectional shape that is one of a v-shape, u-shape, and a box-like shape.

97. The spinal implant of claim 1, wherein said implant has a width and a height, the width of said implant being greater than the height.

98. The spinal implant of claim 1, wherein said forward facet, said rearward facet, and said opposed side facets each form a triangle.

99. The spinal implant of claim 1, wherein said upper and lower surfaces each include a plurality of openings to permit bone growth from adjacent vertebral body to adjacent vertebral body through said implant.

100. The spinal implant of claim 3, wherein said implant has a width and a height, the width of said implant being greater than the height.

101. The spinal implant of claim 3, wherein said forward facet, said rearward facet, and said opposed side facets each form a triangle.

102. The spinal implant of claim 3, wherein said upper and lower surfaces each include a plurality of openings to permit bone growth from adjacent vertebral body to adjacent vertebral body through said implant.

103. The spinal implant of claim 1, wherein said converging sides of said rear facet form an apex having an included angle greater than 90 degrees between said converging sides.

104. The spinal implant of claim 1, wherein said forward facet is directed only toward the leading end.

105. The spinal implant of claim 1, wherein said at least one surface projection has a base, the maximum height being less than a length of said base.

106. The spinal implant of claim 3, wherein said converging sides of said rearward facet are arranged to form an apex having an included angle greater than 90 degrees.

107. The spinal implant of claim 3, wherein said forward facet is directed only toward the leading end.

108. The spinal implant of claim 3, wherein said at least one first and second surface projections each have a maximum height that is less than a length of said base.

109. The spinal implant of claim 1, wherein said at least one surface projection has a base with a maximum width greater than the maximum height.

110. The spinal implant of claim 3, wherein said base of said first and second surface projections has a maximum height and a maximum width greater than the maximum height.

* * * * *

UNITED STATES PATENT AND TRADEMARK OFFICE
CERTIFICATE OF CORRECTION

| | | |
|---|---|---|
| PATENT NO. | : 7,972,381 B2 | Page 1 of 1 |
| APPLICATION NO. | : 10/683071 | |
| DATED | : July 5, 2011 | |
| INVENTOR(S) | : Gary K. Michelson | |

It is certified that error appears in the above-identified patent and that said Letters Patent is hereby corrected as shown below:

Column 11:
Claim 1, Line 47: Change "height, in" to -- height in --.

Column 12:
Claim 2, Line 14: change "toward One" to -- toward one --;
Claim 2, Line 16: change "said implant said" to -- said implant, said --; and
Claim 3, Line 30: change "trailing end spaced" to -- trailing end, spaced --.

Column 14:
Claim 33, Line 3: change "The: spinal" to -- The spinal --;
Claim 46, Line 49: change "to forma" to -- to form a --; and
Claim 53, Line 66: change "at, least" to -- at least --.

Column 15:
Claim 63, Line 20: Change "Thespinal" to -- The spinal --.

Column 16:
Claim 79, Line 1: Change "comprising at," to -- comprising at --.

Signed and Sealed this
Twenty-third Day of August, 2011

David J. Kappos
*Director of the United States Patent and Trademark Office*